United States Patent

Okamura et al.

[11] Patent Number: 5,989,855
[45] Date of Patent: Nov. 23, 1999

[54] BILE ACID CONVERTING MICROORGANISM AND PROCESS FOR PREPARING BILE ACID

[75] Inventors: Akio Okamura; Hiroyuki Matsui, both of Tokyo, Japan

[73] Assignee: Tokyo Tanabe Company Limited, Tokyo, Japan

[21] Appl. No.: 09/155,232

[22] PCT Filed: Mar. 21, 1997

[86] PCT No.: PCT/JP97/00937

§ 371 Date: Sep. 29, 1998

§ 102(e) Date: Sep. 29, 1998

[87] PCT Pub. No.: WO97/36997

PCT Pub. Date: Sep. 10, 1997

[30] Foreign Application Priority Data

Mar. 29, 1996 [JP] Japan .................................. 8-077945

[51] Int. Cl.$^6$ .............................. C12N 1/14; C12P 33/06
[52] U.S. Cl. .......................... 435/58; 435/52; 435/256.3; 435/911
[58] Field of Search ................. 435/52, 58, 911, 435/256.3

[56] References Cited

U.S. PATENT DOCUMENTS

| | | | |
|---|---|---|---|
| 4,579,819 | 4/1986 | Sawada et al. | 435/58 |
| 4,604,353 | 8/1986 | Sawada et al. | 435/911 |

OTHER PUBLICATIONS

Carlstrom et al, "Microbial synthesis of 1β– and 15β–hydroxylated bile acids," Journal of Lipid Research, vol. 22, pp. 1225–1234 (1981).

Joannou et al, "Identification of 15β–hydroxylated $C_{21}$ steriods in the neo–natal . . .," Journal of Steroid Biochemistry, vol. 14, pp. 901–912 (1981).

Computer JPOABS 60–228500 Kimura et al, Nov. 13, 1985.

*Primary Examiner*—Herbert J. Lilling
*Attorney, Agent, or Firm*—Nixon & Vanderhye

[57] ABSTRACT

A microorganism having a capability of introducing a 7β-hydroxyl group into a 7-unsubstituted bile acid, and a process for preparing a bile acid having a 7β-hydroxyl group characterized by bringing the above microorganism into contact with a 7-unsubstituted bile acid to convert the acid to a bile acid having a 7β-hydroxyl group. The process permits ursodeoxycholic acid useful as a cholagogue and intermediates therefor to be efficiently prepared.

7 Claims, 1 Drawing Sheet

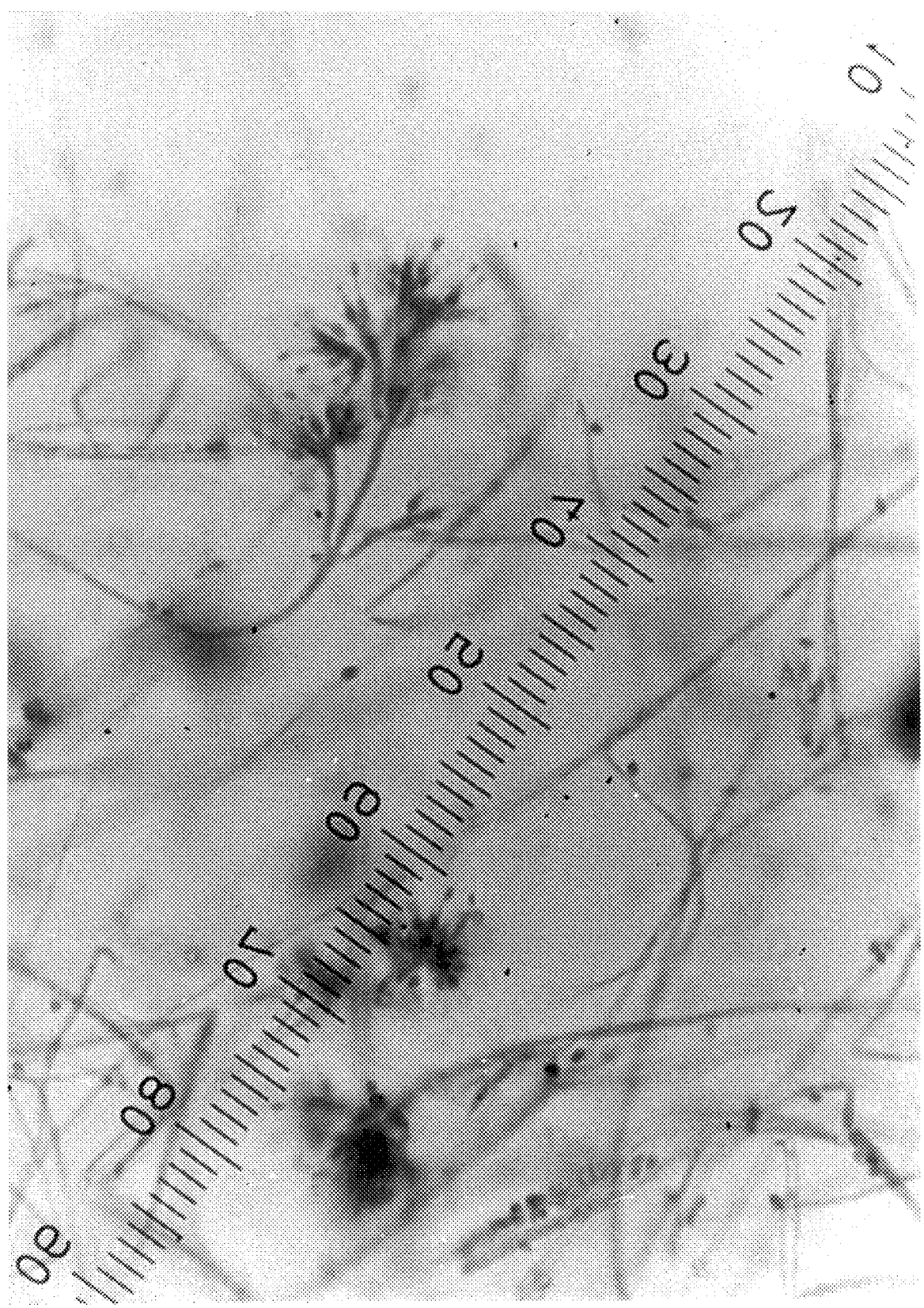
Fig.1  ⊢———⊣ 25 µm

BILE ACID CONVERTING MICROORGANISM AND PROCESS FOR PREPARING BILE ACID

TECHNICAL FIELD

The present invention relates to a microorganism producing a bile acid having a 7β-hydroxyl group such as 3α, 7β-dihydroxy-5β-cholanic acid (hereinafter, referred to as ursodeoxycholic acid) or the like, which is useful as a cholagogue, and to a process for preparing ursodeoxycholic acid or a bile acid having a 7β-hydroxyl group, which is an intermediate for preparing the former, utilizing the microorganism.

BACKGROUND ART

For introducing a 7β-hydroxyl group into a 7-unsubstituted bile acid utilizing the conversion by a microorganism, the following methods have been known:

1) A process for preparing 3α, 7β, 12α-trihydroxy-5β-cholanic acid (hereinafter, referred to as ursocholic acid) from 3α, 12α-dihydroxy-5β-cholanic acid (hereinafter, referred to as deoxycholic acid) using one or more microorganisms belonging to the genus Pleurotus, the genus Coriolus, the genus Daedaleopsis, the genus Panaeolus, the genus Marasmius, the genus Crinipellis, the genus Pholiota or the genus Fusarium. (Japanese Patent Publication No. 34038 of 1989)

2) A process for preparing ursodeoxycholic acid from 3α-hydroxy-5β-cholanic acid (hereinafter, referred to as lithocholic acid) using a microorganism belonging to the genus Fusarium. (Japanese Patent Publication No. 29397 of 1991)

3) A process for preparing a conjugated form of ursodeoxycholic acid from a conjugated form of lithocholic acid using a microorganism belonging to the genus Mortierella. (Japanese Patent Publication No. 29438 of 1993)

When a 7β-hydroxyl group was introduced using these microorganisms, however, it was necessary to adjust the concentration of a substrate at a level as low as approximately 0.02–0.1% v/w. Therefore, a great technical problem arose that a colossal apparatus for production was required when production at an industrial scale was carried out.

On the other hand, microorganisms of the genus Penicillium have been known having a bile acid-converting capacity by introducing a 1β-hydroxyl group and a 15β-hydroxyl group (Journal of Lipid Research, Vol. 22, p. 1225 (1981)); no microorganism of the genus Penicillium, however, has been known to have a bile acid-converting capacity by introducing a 7β-hydroxyl group.

DISCLOSURE OF INVENTION

The purpose of the present invention is to provide an industrially useful process for preparing a bile acid having a 7β-hydroxyl group by obviating the defect in the conventional art where it requires a low concentration for a substrate. After conducting extensive studies for attaining this purpose, the present inventors have found a novel microorganism having a bile acid-converting capacity by introducing a 7β-hydroxyl group, having confirmed that this microorganism introduces a hydroxyl group to the 7β-position of a bile acid at a substrate concentration higher than the conventional one, that is, even at a substrate concentration as high as 0.5% v/w or above, and thus have completed the present invention.

The present invention provides Penicillium sp. TTUR 422 belonging to the genus Penicillium and having a capability of introducing a 7β-hydroxyl group into a 7-unsubstituted bile acid (hereinafter, referred to as TTUR 422), and a process for the preparation of a bile acid having a 7β-hydroxyl group which comprises bringing TTUR 422 into contact with a 7-unsubstituted bile acid to convert the acid to a bile acid having a 7β-hydroxyl group. As shown by the Chemical Reaction 1, deoxycholic acid is converted into ursocholic acid and 12-keto-ursodeoxycholic acid, intermediates for preparing ursodeoxycholic acid, and lithocholic acid is converted into ursodeoxycholic acid, by bringing TTUR 422 into contact with deoxycholic acid or lithocholic acid.

Chemical Reaction 1

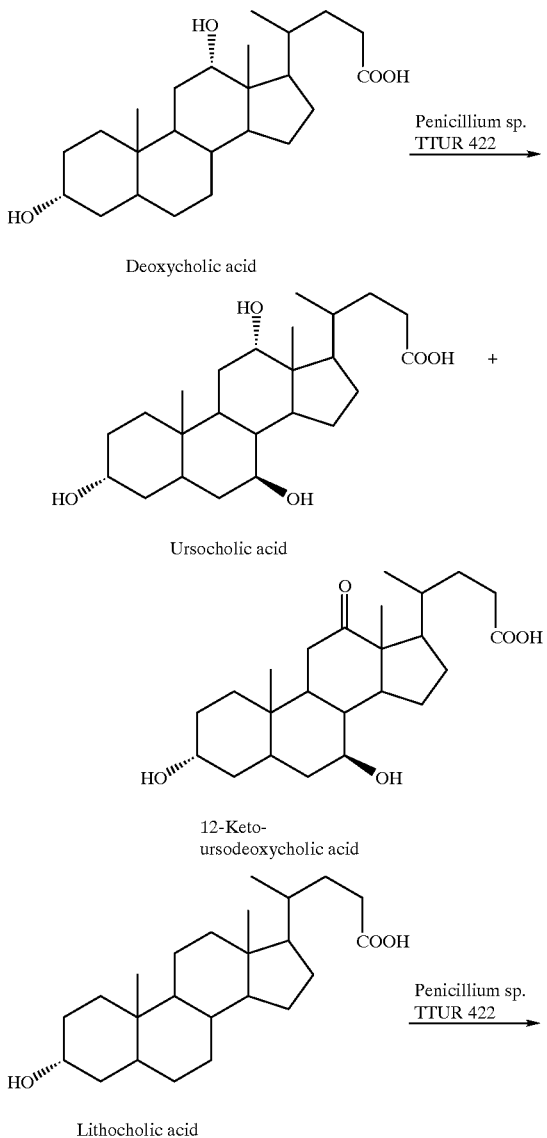

Deoxycholic acid

Ursocholic acid

12-Keto-ursodeoxycholic acid

Lithocholic acid

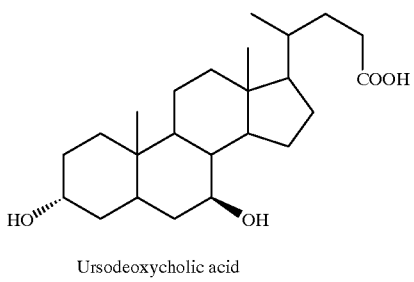

Ursodeoxycholic acid

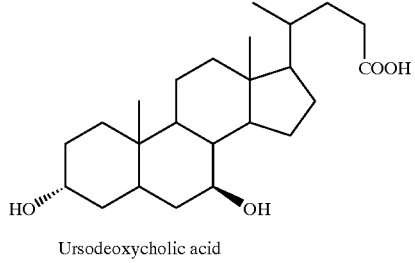

Ursodeoxycholic acid

Ursocholic acid obtained by the present invention is converted into 12-keto-ursodeoxycholic acid by oxidizing the hydroxyl group at the 12-position according to a chemical process using an oxidizing agent or a process using a microorganism (Japanese Laid-open Patent Publication No. 111391 of 1993).

Then, ursodeoxycholic acid is obtained at a satisfactory yield by subjecting 12-keto-ursodeoxycholic acid to Wolff-Kishner reduction.

Chemical Reaction 2

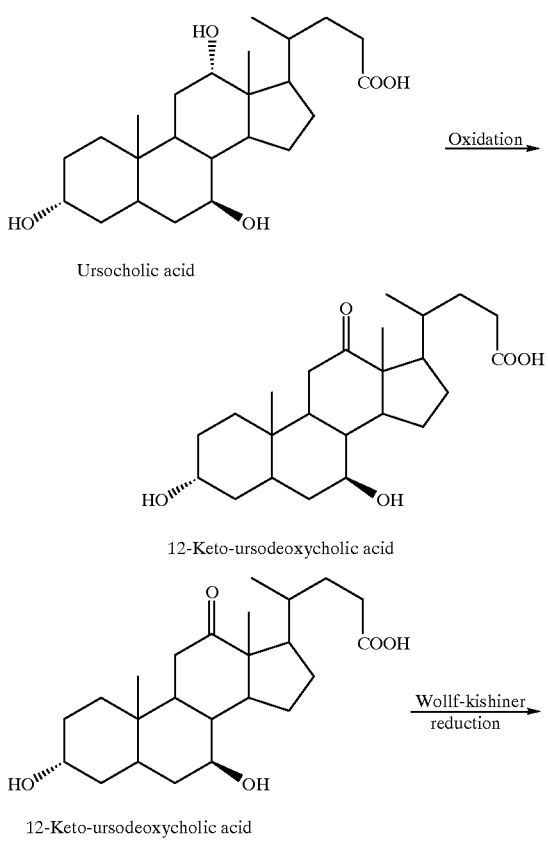

Specific examples of the invention are illustrated below but it should be appreciated that the preparation process of the present invention is not limited to these examples only.

(1) A process in which TTUR 422 is cultured in a medium containing a 7-unsubstituted bile acid to convert the acid to a bile acid having a 7β-hydroxyl group, which is then obtained.

(2) A process in which TTUR 422 is cultured in a nutrition medium, and after separating TTUR 422 from the medium by centrifugation, filtering by a filter paper, etc.; cells are brought into contact with a 7-unsubstituted bile acid in an appropriate reaction solution to convert the acid to a bile acid having a 7β-hydroxyl group, which is then obtained.

(3) A process in which, after immobilizing TTUR 422 separated in the process (2) on a carrier such as polyacrylamide, calcium alginate or the like, the carrier is brought into contact with a reaction solution containing a 7-unsubstituted bile acid to convert the acid to a bile acid having a 7β-hydroxyl group, which is then obtained.

(4) A process in which, after culturing TTUR 422 in a nutrition medium until spores are formed and then collected, the spores are placed in a reaction solution in which a 7-unsubstituted bile acid is dissolved or suspended to convert the acid to a bile acid having a 7β-hydroxyl group, which is then obtained.

(5) A process in which, after immobilizing spores collected in process (4) in a manner similar to cells in (3), the spores are brought into contact with a reaction solution containing a 7-unsubstituted bile acid to convert the acid to a bile acid having a 7β-hydroxyl group, which is then obtained.

In process (1), 7-unsubstituted bile acid can be added appropriately during the culturing step.

In addition, in the above-described processes (2), (3), (4) and (5), it is desirable to add organic substances as an energy source, for example, glucose, other carbohydrates, casein hydrolysate or yeast extract, at a low concentration to the reaction solution.

The 7-unsubstituted bile acid includes, for example, lithocholic acid, deoxycholic acid, 3α-hydroxy-12-keto-5β-cholanic acid (hereinafter, referred to as 12-keto-lithocholic acid) and the like. The microorganism according to the present invention has the capability of converting these substrate bile acids into bile acids having a 7β-hydroxyl group but does not show a property of assimilating or decomposing these substrate bile acids.

The concentration of the substrate is more than 0% v/w and 5% v/w or less (0–5% v/w), preferably 0.5% v/w or more and 3% v/w or less (0.5–3% v/w), and more preferably 0.5% v/w or more and 1% v/w or less (0.5–1% v/w).

The growth morphology of TTUR 422, the microorganism of the present invention, in media is illustrated as follows:

(1) Growth Morphology in Various Media

When TTUR 422 was cultured in the oatmeal agar medium (ISP medium, No. 3) at 25° C. for 7 days, white wooly colonies having a diameter of 2.5–3.5 cm were formed with synnema-like structure (synnema (Synnema: spores are formed covering a stem) or coremia (Coremia: characterized by a stem without spore and a compact oval-shaped top part)) of concentric circles having a height of 1–5 mm. Conidia were yellowish gray (No. 68 in Today's color/300 by Nippon Shikisai Sha). Yellowish red (No. 15 in Today's color/300 by Nippon Shikisai Sha) secretions were observed in places. At the reverse side, only the color of the medium was confirmed.

Growth on Czapek's agar medium was somewhat slow, and white wooly colonies having a diameter of 2.0–2.5 cm were formed upon the culture at 25° C. for 7 days. The reverse side was white.

(2) Morphological Characteristics

FIG. 1 shows a micrograph (magnification: 400 times) of the growth morphology of TTUR 422 when cultured at 27° C. for a week with Miura's medium (1 g of glucose, 1 g of potassium dihydrogen phosphate, 0.2 g of magnesium sulfate (heptahydrate), 0.2 g of potassium chloride, 2.0 g of sodium nitrate, 0.2 g of yeast extract, 13 g of agar, and 1 liter of tap water; pH 6.5–7.0). Conidiophores were formed on the surface of the mycelium and synnemata, when formed, were present at the upper part of the mycelium. The conidiophores were usually compound-verticillate but sometimes irregularly branched. The number of metula was 2 or 3 and their size was 5–7×1.5–2.5 μm. The number of phialide was 3 per metula and their size was 8–11×1.0–2.0 μm, with the shape being long and slender at the top, slender at the foot and warped ampoule-shaped at the middle. The spores were spindle-shaped and their size was 3.0–4.0×1.0–2.0 μm. No sexual generation was observed upon a long-term culture. From the above-described morphological characteristics, the isolated strain was identified as a strain belonging to the genus Penicillium.

Attempts have been made to identify TTUR 422 referring to the classification of the genus Penicillium by Pitt (John I. Pitt, The genus Penicillium and its telemorphic states Eupenicillium and Talaromyces, Academic Press, London, New York, Toronto, Sydney, San Francisco (1979)). Upon a culture of the isolated strain on various media including PDA, ISP No.3, CYA (Czapek yeast autolysate agar: Pitt, 1973), MEA (Malt extract agar) and others, synnemata were formed within 7 days. Species from genus Penicillium displaying such morphology include 3 species: *Penicillium claviforme*, *Penicillium isariiforme* and *Penicillium duclauxii*. Comparison of the species gave the following results:

1) The synnema of TTUR 422 formed was similar to synnema of *isariiforme* or *duclauxii* rather than coremia of *claviforme*.

2) The comparison of the size of colonies from 3 Penicillium species (*Penicillium claviforme*, *Penicillium isariiforme* and *Penicillium duclauxii*) was as follows:

I. CYA medium

When cultured at 25° C., the size of colonies from TTUR 422 was smaller than those from *isariiforme* and *claviforme*, and larger than that from *duclauxii*. At 5° C., *claviforme* grew to the size of several millimeters but TTUR 422, *isariiforme* and *duclauxii* showed almost no growth. At 30° C., no species grew.

II. G25N medium (25% glycerol nitrate agar, Pitt, 1973)

When cultured at 25 ° C., *claviforme* grew to a size exceeding 10 mm in diameter but TTUR 422, *isariiforme* and *duclauxii* only grew to several millimeters.

III. MEA medium

Growth of *isariiforme* was larger than the others.

The size of colony was similar to that of *duclauxii* in general.

3) The formed colonies showed various morphologies depending on the kind of media, and the color of the conidia was different as shown in Table 1.

TABLE 1

Color of conidia in various media

| | ISP No.3 | CYA | MEA |
|---|---|---|---|
| TTUR 422 | pink-white (No. 50) | pink-white (No. 50), yellowish gray (No. 68) | pink-white (No. 104) |
| claviforme ATCC48945 | olive green (No. 128) | Pale yellow-brown (No. 94) | grayish yellow-green (No. 130) |
| isariiforme ATCC48951 | dull yellow-green (No. 135) | yellowish white (No. 106) | deep yellow (No. 108) |
| duclauxii ATCC9121 | yellow-brown (No. 101) | olive green (No. 128) | yellowish red (No. 15), olive green (No. 128) |

The color of conidia from TTUR 422 was light in color such as pink-white (No. 50) and yellowish gray in above three media. The color of conidia from *claviforme*, *isariiforme* and *duclauxii* had a tendency towards deep color such as olive green (No. 128), grayish yellow-green (No. 130), dull yellow-green (No. 135) and yellow-brown (No. 101).

4) Morphology under microscope

Penicilli (Penicilli:Penicillus) of TTUR 422 were formed like a blooming flower as shown in FIG. 1 and showed a characteristic morphology having many curved ampoule-shaped radial phialides. On the other hand, penicilli of *claviforme*, *isariiforme* and *duclauxii* were formed directed towards the top and no shape of phialide characteristic in TTUR 422 was observed. In addition, the conidium of TTUR 422 had a shape of an oval narrower than those of *claviforme*, *isariiforme* and *duclauxii*.

Since TTUR 422 had one characteristic partly different from all other species as described above, it was confirmed to be a novel species belonging to the genus Penicillium and forming synnema.

Therefore, this strain was deposited in Name: National Institute of Bioscience and Human-Technology Agency of Industrial Science and Technology, Ministry of Industrial Trade and Industry, Address: 1-3, Higashi 1-chome, Tsukuba-shi, Ibaragi-ken, Japan (Postal Zip-code: 305) on Feb. 22, 1996, as Penicillium sp. TTUR 422 (Deposition Number: FERM BP-5410).

The physiological properties of the strain TTUR 422 are as follows:

(1) Optimum growth condition (pH and temperature)

The optimum growth pH is 5–6, and the optimum growth temperature is 25–27° C.

(2) Viable range (pH and temperature)

The range of pH is 3–9, and the range of temperature is 5–29° C.

(3) Other remarkable characteristics

1) Synnemata were formed within 7 days of culture.

2) Liquid culture shows a yeast-like growth.

Now, picking up of TTUR 422 is described below. From soils at various places in the Kanto area were isolated molds growing on PDA plate medium supplemented with 5% v/w sodium cholate. They were inoculated independently in middle-sized test tubes (18φ×180 mm) containing 5 ml of a medium for testing capacity of conversion, and cultured at 28° C. for 7 days with shaking. At the end of culturing, the strains were screened for capacity of converting deoxycholic acid into ursocholic acid by qualitatively analyzing the liquid media with thin layer chromatography in order to compare them with an authentic sample of ursocholic acid.

The medium for testing capacity of conversion contained 24 g of potato dextrose broth, 5 g of yeast extract and 5 g of sodium deoxycholic acid as a substrate for conversion reaction in 1 liter of de-ionized water, and adjusted to pH 7.5.

As the result, TTUR 422 was obtained as a strain isolated from soil collected at Kitamoto-shi, Saitama-ken, on Aug. 9, 1993, and having the best capacity for converting deoxycholic acid into ursocholic acid.

BRIEF DESCRIPTION OF THE DRAWING

FIG. 1 is a micrograph showing the morphology of TTUR 422.

MODE FOR CARRYING OUT THE INVENTION

The examples of the present invention will now be described by embodiments, which should not be construed as a limitation upon the scope of the present invention.

<Embodiment 1>

Into a 5 liter fermenter was placed 2.5 liter of a liquid medium (containing 10 g of glucose, 20 g of special grade Esusan meat (soybean protein, manufactured by Ajinomoto), 10 g of yeast extract and 10 g of deoxycholic acid (substrate concentration; 1% v/w) in 1 liter of water) adjusted to pH 7.5 with 4N-NaOH. The liquid medium in the abovementioned fermenter was inoculated with 25 ml of a culture solution of TTUR 422 which was previously cultured with shaking in a medium composed of 0.4% potato extract, 2% glucose and 0.5% yeast extract at 27° C. for 2 days. The inoculation was aerobically cultured with a stirring velocity of 300 rpm and an aeration rate of 2.5 l/minutes for 7 days, adjusting at a culturing temperature of 27° C. and pH of 7.5.

Upon termination of the culturing, cells were removed by centrifugation, and the culture solution was extracted thrice with twice the amount of ethyl acetate after adjusting pH to 3 with hydrochloric acid. The ethyl acetate layer was washed several times with water and dried over anhydrous sodium sulfate. Ethyl acetate was evaporated under reduced pressure to give 24.5 g of crystals. To a column (2.2 cm in diameter and 70 cm in height) packed with 95 g of silica gel (FL60D, manufactured by Fuji Silicia Chemicals) was applied 1 g of the crystals, and the column was then fractionally eluted using eluents consisting of the mixed solvents described below in exact order. Fractions showing each spot of 12-keto-ursodeoxycholic acid and ursocholic acid on TLC analysis were collected and evaporated to give 367 mg of 12-keto-ursodeoxycholic acid and 88 mg of ursocholic acid in crystals respectively.

(Eluents)
1) chloroform:acetone:acetic acid=8:2:0.3, 500 ml
2) chloroform:acetone:acetic acid=7:2:0.5, 600 ml
3) chloroform:acetone:acetic acid=7:2:1, 600 ml
4) chloroform:acetone:acetic acid=3:1:1, 600 ml
5) chloroform:acetone:acetic acid=1:1:1, 600 ml The fact that the conversion products were ursocholic acid and 12-keto-ursodeoxycholic acid was confirmed by agreement of Rf values in TLC analysis, retention times in HPLC analysis, NMR spectra and mass analysis values for authentic samples of both ursocholic acid and 12-keto-ursodeoxycholic acid and values for the conversion products.

Conditions for TLC Analysis and Rf Values Thereof
  Carrier; Kieselgel 60 (0.25 mm in thickness, manufactured by Merck)
  Developing solvent 1; chloroform:acetone:acetic acid= 7:2:1 (volume ratio)
  Developing solvent 2; benzene:isopropanol:acetic acid= 40:10:1 (volume ratio)
  Coloring; Coloring is effected by spraying the phosphorus molybdic acid-sulfuric acid reagent (a reagent prepared by dissolving 1 g of phosphorus molybdic acid in 20 ml of methanol and adding 1 ml of concentrated sulfuric acid) and heating until the spot of the bile acid becomes deep blue.

Rf Values
  Developing solvent 1: ursocholic acid: authentic sample/ Embodiment 1=0.14/0.14
  Developing solvent 1: 12-keto-ursodeoxycholic acid: authentic sample/Embodiment 1=0.25/0.25
  Developing solvent 2: ursocholic acid: authentic sample/ Embodiment 1=0.24/0.24
  Developing solvent 2: 12-keto-ursodeoxycholic acid: authentic sample/Embodiment 1=0.38/0.38

Conditions for HPLC Analysis and Retention Times Thereof
  Column; Inertsil ODS column (column size: 4.6φ×250 mm)
  Detection; differential refraction
  Mobile phase; 0.03 M $Na_2HPO_4$ buffer (adjusted to pH 3 with $H_3PO_4$):
  acetonitrile: methanol=37:30:40
  Flow rate of mobile phase; 1 ml/minute
  Retention time; ursocholic acid: authentic sample/ Embodiment 1=8.0 minutes/8.0 minutes
  12-keto-ursodeoxycholic acid: authentic sample/ Embodiment 1=6.1 minutes/6.1 minutes $^1$H-NMR spectrum (DMSO-d6, ppm)
  12-keto-ursodeoxycholic acid
    0.77 (3H, d, J=6.1 Hz), 0.99 (6H, s), 3.32 (2H, s), 4.13 (1H, d, J=6.7 Hz), 4.44 (1H, d, J=4.9 Hz), 11.93 (1H, s)
  Ursocholic Acid
    0.60 (3H, d, J=6.1 Hz), 0.85 (3H, s), 0.92 (3H, s), 3.33 (2H, br), 3.76 (1H, s), 3.82 (1H, d, J=6.7 Hz), 4.18 (1H, d, J=3.7 Hz), 4.46 (1H, d, J=4.3 Hz), 11.94 (1H, s)

Mass Analysis Value (LC/MS, Mode: APCI, $MH^+$)
  APCI (m/z); ursocholic acid: authentic sample/ Embodiment 1=409/409
  12-keto-ursodeoxycholic acid: authentic sample/ Embodiment 1=407/407

Molecular weight; ursocholic acid: authentic sample/ Embodiment 1=408/408
  12-keto-ursodeoxycholic acid: authentic sample/ Embodiment 1=406/406

<Embodiment 2>

Conversion was carried out according to Embodiment 1 with the same strain and the same medium but using 12-keto-lithocholic acid (substrate concentration; 1% v/w) in place of the substrate deoxycholic acid to give 24.6 g of the conversion product. HPLC analysis conducted under the conditions described in Embodiment 1 showed that the composition ratio of 12-keto-ursodeoxycholic acid in the conversion product was 43.9%.

Silica gel column chromatography was carried out in a manner similar to that in Embodiment 1 using 1 g sample of the conversion product. As a result, 395 mg of 12-keto-ursodeoxycholic acid was obtained showing a purity of 97.6% by HPLC analysis.

The fact that the conversion product was 12-keto-ursodeoxycholic acid was confirmed, because Rf value in TLC analysis, retention time in HPLC analysis, NMR spectrum and mass analysis value for an authentic sample of 12-keto-ursodeoxycholic acid and the conversion product agreed with the values described in Embodiment 1.

<Embodiment 3>

Conversion was carried out according to Embodiment 1 with the same strain and the same medium but using lithocholic acid, in an amount of 5 g per 1 liter (substrate concentration; 0.5% v/w), in place of the substrate deoxycholic acid to give 24.7 g of the conversion product. HPLC analysis conducted under the conditions described below showed that the composition ratio of ursodeoxycholic acid in the conversion product was 5.1%.

Silica gel column chromatography was carried out in a manner similar to that in Embodiment 1 using 1 g sample of the conversion product. As the result, 46 mg of ursodeoxycholic acid was obtained showing a purity of 97.6% by HPLC analysis.

The fact that the conversion product was ursodeoxycholic acid was confirmed by agreement of Rf value in TLC analysis, retention time in HPLC analysis, NMR spectrum and mass analysis value for authentic sample of ursodeoxycholic acid and values for the conversion product.

Conditions for TLC Analysis and Rf Values Thereof
  Conditions for analysis; the same as in Embodiment 1
  Rf Values
  Developing solvent 1; ursodeoxycholic acid: authentic sample/Embodiment 3=0.38/0.38
  Developing solvent 2; ursodeoxycholic acid: authentic sample/Embodiment 3=0.42/0.42

Conditions for HPLC Analysis and Observed Retention Times
  Conditions for analysis; the same as in Embodiment 1
  Retention time; ursodeoxycholic acid: authentic sample/Embodiment 3=18.5 minutes/18.5 minutes $^1$H-NMR spectrum (DMSO-d6, ppm)
  0.62 (3H, s), 0.87 (3H, s), 0.89 (3H, s), 3.33 (2H, s), 3.87 (1H, d, J=6.7 Hz), 4.43 (1H, d, J=4.3 Hz), 11.93 (1H, s)

Mass Analysis Value (LC/MS, Mode: APCI, MH$^+$)
  APCI (m/z); ursodeoxycholic acid: authentic sample/Embodiment 4=393/393
Molecular weight; ursodeoxycholic acid: authentic sample/Embodiment 3=392/392

INDUSTRIAL APPLICABILITY

As described above, the microorganism according to the present invention enables introduction of a hydroxyl group into the 7β-position of a bile acid at a higher substrate concentration as compared to the conventional microorganism, and by utilizing the microorganism, 3α,7β-dihydroxy-5β-cholanic acid, which is useful as a cholagogue, or preparing intermediates thereof can be produced with good efficiency.

What is claimed is:

1. Penicillium sp. TTUR 422 (FERM BP-5410) in isolated form belonging to the genus Penicillium and having a capability of introducing a 7β-hydroxyl group into a 7-unsubstituted bile acid.

2. A process for preparation of a bile acid having a 7β-hydroxyl group which comprises bringing a microorganism, belonging to the genus Penicillium and having a capability of introducing a 7β-hydroxyl group into a 7-unsubstituted bile acid, into contact with a 7-unsubstituted bile acid to convert the acid to a bile acid having a 7β-hydroxyl group.

3. The process for preparation according to claim 2, wherein the 7-unsubstituted bile acid is deoxycholic acid, 12-keto-lithocholic acid or lithocholic acid.

4. The process for preparation according to claim 2, wherein the concentration of 7-unsubstituted bile acid is 0–5% v/w when the acid is brought into contact with the microorganism.

5. The process for preparation according to claim 2, wherein the concentration of 7-unsubstituted bile acid is 0.5–3% v/w when the acid is brought into contact th the microorganism.

6. The process for preparation according to claim 2, wherein the concentration of 7-unsubstituted bile acid is 0.5–1% v/w when the acid is brought into contact with the microorganism.

7. The process for preparation according to claim 2, wherein the microorganism belonging to the genus Penicillium and having a capability of introducing a 7β-hydroxyl group into a 7-unsubstituted bile acid is Penicillium sp. TTUR 422 (FERM BP-5410).

* * * * *